United States Patent [19]

Joiner

[11] Patent Number: 5,662,954
[45] Date of Patent: Sep. 2, 1997

[54] METHOD FOR PREPARING MINERAL-ENRICHED CITRATE COMPOSITIONS

[76] Inventor: Margie Joiner, c/o Howard Johnson, #613, US Highway 11&80, Meridian, Miss. 39302

[21] Appl. No.: 651,222

[22] Filed: May 22, 1996

Related U.S. Application Data

[63] Continuation-in-part of Ser. No. 270,283, Jul. 5, 1994, abandoned.

[51] Int. Cl.$^6$ .................... A23L 1/304; A23P 1/04
[52] U.S. Cl. .................... 426/74; 426/72; 426/97; 426/99; 426/384; 426/599
[58] Field of Search .................... 426/72, 74, 599, 426/384, 97, 99

[56] References Cited

U.S. PATENT DOCUMENTS

| | | |
|---|---|---|
| 4,772,467 | 9/1988 | Pak . |
| 4,814,177 | 3/1989 | Walsdorf et al. . |
| 5,053,238 | 10/1991 | Zeidler et al. . |
| 5,149,552 | 9/1992 | Vidal et al. . |
| 5,219,602 | 6/1993 | Saleeb et al. . |

FOREIGN PATENT DOCUMENTS

| | | |
|---|---|---|
| 0016576 | 1/1985 | Japan . |
| 16576 | 1/1985 | Japan . |
| 100185 | 5/1986 | Japan . |
| 91164 | 4/1987 | Japan . |
| 67157 | 3/1989 | Japan . |
| 153937 | 6/1993 | Japan . |

*Primary Examiner*—Helen Pratt
*Attorney, Agent, or Firm*—David H. Semmes

[57] ABSTRACT

Method for preparing mineral-enriched citrate compostions for enhancement of fingernail growth. Lemon or lime juice are reacted with the shells of raw fresh eggs to extract minerals such as calcium carbonate, calcium citrate, as well as trace minerals. The enriched citrate composition is particularly useful in enhancing growth of fingernails.

1 Claim, No Drawings

METHOD FOR PREPARING MINERAL-ENRICHED CITRATE COMPOSITIONS

CROSS-REFERENCE TO RELATED APPLICATIONS

A Continuation-in-Part of METHOD FOR PREPARATION OF CALCIUM-ENRICHED CITRATE COMPOSITIONS AND PRODUCTS THEREOF (Ser. No. 08/270,283), filed Jul. 5, 1994, now abandoned.

BACKGROUND OF THE INVENTION

This invention is related to the method of manufacture of mineral-enriched citrate compositions, wherein one obtains by lemon juice extraction at least some or all of the minerals contained in the shell of raw fresh eggs. The shell is removed from the egg and processed by the lemon citrate juice. Specifically, lemon juice derivatives such as calcium carbonate, calcium citrate, magnesium carbonate, magnesium citrate and tri-calcium phosphate, tri-calcium citrate are processed to create a mineral-enriched citrate composition. The lemon juice, which is thus enriched with extracted eggshell minerals, may be made available as powdered concentrate. In some applications, lime juice may be substituted for lemon juice. The product is particularly useful in enhancing growth of finger nails.

THE PRIOR ART

| INVENTOR | PATENT NO. |
|---|---|
| SALEEB et al. | 5,219,602 |
| VIDAL et al. | 5,149,522 |
| ZEIDLER et al. | 5,053,238 |
| WALSDORF et al. | 4,814,177 |
| PAK | 4,772,467 |
| Japan: | |
| SUGITANI | 60-16576 |
| KUSHIBIKI | 100185 |
| SHINA | 6291164 |
| UEDA | 153937 |
| SHINA | 01-67157 |

While vinegar will also dissolve egg shell it does not produce the desired end product: calcium citrate. Vinegar is acetic acid and would produce an acetate salt. In order to be effective, calcium must be absorbed by the intestines. Calcium citrate has been shown to be superior to other calcium salts such as calcium carbonate, calcium oxalate, calcium oxide. Calcium citrate is most efficient in its absorption in the intestines. From there, of course, it goes into the bloodstream to be delivered to the target organs, teeth, bones, nails, as well as to participate in other bodily biochemistries. The goal is not just to dissolve egg shell, but to produce an effective end product.

The patents of PAK and WALSDORF et al. describe the production of calcium citrate dietary supplement which is made from calcium carbonate (dry chemical) and citric acid (also dry chemical). In the background to the invention, the superior absorptivity of calcium as the citrate salt is explained and references.

However PAK and WALSDORF do make use of the same chemical reaction as Applicant does, namely the reaction of calcium carbonate with citric acid to form calcium citrate and carbon dioxide and water:

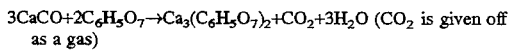
($CO_2$ is given off as a gas)

Applicant's product also provides additional constituents from both the shell and the juice which are involved in calcium uptake, namely isocitric and ascorbic acids. Also provided by Applicant's product is a variety of other trace minerals, namely manganese, magnesium iron, potassium and phosphorous. All are utilized by the body for nail growth.

Applicant does not use binders or carriers to form tablets. Binders and carriers interfere with absorption because they are hard to digest in the stomach. Tablets and pills are often excreted without complete digestion.

Applicant's product is freeze dried. Water is removed by freezing the final liquid and then pulling a very strong vacuum on it. This is a variation of Boyle's law. Liquids will go to the gas phase at the right combination or pressure and temperature. Water "boils"—goes to a gas—by heating it to 212° F. at atmospheric pressure. Lower the pressure—pull a vacuum—and the temperature required to vaporize water also goes down. Freeze drying takes water from the solid phase (ice) directly to the gas phase by reducing the pressure and temperature substantially. Without added heat, the integrity of Applicant's product is preserved. Heat destroys ascorbic acid.

Applicant's end product is a mineral-enriched citrate composition. SUGITANI's end product is a mayonnaise with unreacted eggshells suspended therein. Ingesting SUGITANI's mayonnaise will not enhance nail growth. In SUGITANI there is not enough of the lemon/shell reaction product and what is there is dispersed in large quantities of oil.

Applicant does not spray dry as taught by VIDAL. Spray drying requires heat. Applicant avoids heat because it destroys certain vitamins, namely ascorbic acid.

Applicant's method of manufacture enhances nail growth because the end product contains large amounts of calcium citrate along with other trace minerals and vitamins necessary for calcium absorption and, consequently, nail growth.

Lemon and lime juice solubilize maximum calcium from egg shells because they contain the most citric acid per unit volume, thereby providing a final product more dense in calcium citrate.

SUMMARY OF THE INVENTION

Process and product for the formulation of an edible composition from reacting lemon or lime juice with fresh eggshells to obtain the minerals: calcium carbonate, manganese carbonate and tri-calcium phosphate, combining the juice and mineral extracts. The resultant product may be used for drinks, powder mixtures and/or capsule concentrate.

DESCRIPTION OF THE PREFERRED EMBODIMENTS

Whereas most fruit juices contain organic acids which have characteristics similar to those of lemon juice or lime juice, none of said organic acids except lemon and lime juice have the efficacy to extract mineral compositions from the raw fresh eggshell. Lemon and lime juice, per se, contain the following organic acids: 1-malic, malic, citric, isocitric, citric/isocitric, 1-ascorbic acid. Likewise, domestic egg shells, per se, contain composite metal salts: calcium carbonate, manganese carbonate and tri-calcium phosphate. To extract the metal salts herein, one employs the extraction characteristics of the lemon or lime juice to solubilize eggshells which have been removed from the egg membranes, the albumen or egg white and the yolk.

The known chemical compositions of lemon juice and lime juice, as well as orange juice, grapefruit juice and apple cider vinegar may be summarized, as follows:

| Chemical Compositions of Juices Used in Eggshell Calcium Extraction Study | | | | | |
|---|---|---|---|---|---|
| In mg/100 g | Lemon Juice | Lime Juice | Orange Juice | Grapefruit Juice | Apple Cider Vinegar |
| Calcium | 7.0 mg | 9.0 mg | 11.0 mg | 9.0 mg | 4.35 mg |
| Iron | 0.03 mg | 0.03 mg | 0.20 mg | 0.20 mg | 0.62 mg |
| Magnesium | 6.0 mg | 6.0 mg | 11.0 mg | 12.0 mg | — |
| Phosphorus | 6.0 mg | 7.0 mg | 17.0 mg | 15.0 mg | — |
| Potassium | 124.0 mg | 109.0 mg | 200.0 mg | 162.0 mg | — |
| Sodium | 1.0 mg | 1.0 mg | 1.0 mg | 1.0 mg | 20.0 mg |
| Vitamin C | 46.0 mg | 29.3 mg | 50.0 mg | 38.0 mg | 0.94 mg |
| Thiamine (B1) | 0.030 mg | 0.020 mg | 0.090 mg | 0.040 mg | — |
| Riboflavin (B2) | 0.010 mg | 0.010 mg | 0.030 mg | 0.020 mg | — |
| Niacin | 0.100 mg | 0.100 mg | 0.400 mg | 0.200 mg | — |
| Moisture | 90.73 g | 90.21 g | 88.30 g | 90.00 g | 98.00 g |
| Protein | 0.38 g | 0.44 g | 0.70 g | 0.50 g | 0.10 g |
| Fat | 0.00 g | 0.10 g | 0.20 g | 0.10 g | 0.03 g |
| Ash | 0.26 g | 0.24 g | 0.40 g | 0.20 g | 1.0 g |
| Cabohydrates | 8.63 g | 9.01 g | 10.40 g | 9.20 g | 0.91 g |
| Energy (kcal) | 25 kcal | 27 kcal | 45 kcal | 39 kcal | 40 kcal |

The following examples depict the invention.

Eggshell Calcium Extraction Study

EXAMPLE I:

Type of Liquid Used: Lemon Juice
Time eggshells were put into liquid: 4:30 p.m. 3/12/96
Time eggshells were removed from liquid: 2:30 p.m. 3/13/96
Total time eggshells were immersed in liquid: 22 hours
Volume of liquid used: 6 quarts
Initial weight of liquid: 11.80 pounds    Weight of eggshells: 294.7 grams
Final weight of liquid: 11.20 pounds    Final weight of eggshells after drying: 255.3 grams
Weight of Extracted eggshell: 39.4 grams    Percent eggshell extracted: 13.37%
Initial pH: 2.31
Final pH: 3.32
Calcium content of liquid rep #1: 602 mg/100 g
Calcium content of liquid rep #2: 607 mg/100 g

EXAMPLE II:

Type of Liquid Used: Stirred Lemon Juice
Time eggshells were put into liquid: 10:00 a.m. 3/16/96
Time stirring was started: 12:07 p.m. 3/16/96
Time eggshells were removed from liquid and stirring stopped: 5:07 p.m. 3/13/96
Total time eggshells were immersed in liquid: 7 hours
Time eggshells were stirred: 5 hours
Volume of liquid used: 500 mL
Initial weight of eggshells: 44.0 grams    Final weight of eggshells after drying: 21.7 grams
Weight of Extracted eggshell: 22.3 grams    Percent eggshell extracted: 50.68%
Initial pH: 2.31
Final pH: 5.88
Calcium content of liquid rep #1: 1500 mg/100 g

EXAMPLE III

Type of Liquid Used: Stirred Lemon Juice
Time eggshells were put into liquid: 4:30 p.m. 3/12/96
Time stirring was started: 4:30 p.m. 3/12/96
Time eggshells were removed from liquid and stirring stopped: 9:30 a.m. 3/13/96
Total time eggshells were immersed in liquid: 17 hours
Time eggshelld were stirred: 17 hours
Volume of liquid used: 385.9 g
Initial weight of eggshells: 21.23 grams    Final weight of eggshells after drying: 0.00 grams
Weight of Extracted eggshell: 21.23 grams    Percent eggshell extracted: 100.00%
Initial pH: 2.31
Final pH: 5.97
Calcium content of liquid rep #1: 2039 mg/100 g

EXAMPLE IV

Type of Liquid Usd: Lime Juice
Time eggshells were put into liquid: 4:30 p.m. 3/12/96
Time eggshells were removed from liquid: 2:30 p.m. 3/13/96
Total time eggshells were immersed in liquid: 22 hours
Volume of liquid used: 6 quarts
Initial weight of liquid: 11.95 pounds    Weight of eggshells: 294.7 grams -continued

Eggshell Calcium Extraction Study

Final weight of liquid: 11.95 pounds   Final weight of eggshells after drying: 252.0 grams
Weight of Extracted eggshell: 42.7 grams   Percent eggshell extracted: 14.49%
Initial pH: 2.36A
Final pH: 3.48
Calcium content of liquid rep #1: 686 mg/100 g
Calcium content of liquid rep #2: 686 mg/100 g

EXAMPLE V:

Type of Liquid Used: Stirred Lime Juice
Time eggshells were put into liquid: 10:00 a.m. 3/16/96
Time stirring was started: 12:07 p.m. 3/16/96
Time eggshells were removed from liquid and stirring stopped: 5:07 p.m. 3/13/96
Total time eggshells were immersed in liquid: 7 hours
Tikme eggshells were stirred: 5 hours
Volume of liquid used: 500 mL
Initial weight of eggshells: 44.0 grams   Final weight of eggshells after drying: 23.6 grams
Weight of Extracted eggshell: 20.4 grams   Percent eggshell extracted: 46.36%
Initial pH: 2.36
Final pH: 5.82
Calcium content of liquid rep #1: 1560 mg/100 g

TABLE 1

Eggshell Calcium Extraction Study Summary (Sedentary Juices)

| | Lemon Juice | Lime Juice | Orange Juice | Grapefruit Juice | Apple Cider Vinegar |
|---|---|---|---|---|---|
| Volume of Liquid | 6 quarts | 6 quarts | 6 quarts | 6 quarts | 6 quarts |
| Initial Weight of Eggshells | 294.7 g | 294.7 g | 294.5 g | 294.6 g | 294.6 g |
| Final Weight of Eggshells | 255.3 g | 252.0 g | 263.0 g | 258.8 g | 125.5 g |
| Weight of Extracted Eggshell | 39.4 g | 42.7 g | 31.5 g | 35.8 g | 169.1 g |
| Percent Eggshell Extracted | 13.37% | 14.49% | 10.70% | 12.15% | 57.40% |
| Initial pH | 2.31 | 2.36 | 3.58 | 3.17 | 3.16 |
| Final pH | 3.32 | 3.48 | 5.02 | 5.18 | 4.78 |
| Calcium Content | 605 mg/100 g | 686 mg/100 g | 289 mg/100 g | 297 mg/100 g | 1280 mg/100 g |

TABLE 2

Eggshell Calcium Extraction Study Summary (Stirred Juices)

| | Lemon Juice | Lime Juice | Orange Juice | Grapefruit Juice | Apple Cider Vinegar |
|---|---|---|---|---|---|
| Volume of Liquid | 500 mL | 500 mL | 500 mL | 500 mL | 500 mL |
| Initial Weight of Eggshells | 44.0 grams | 44.0 grams | 44.0 grams | 44.0 grams | 44.0 grams |
| Final Weight of Eggshells | 21.7 grams | 23.6 grams | 39.9 grams | 36.8 grams | 21.7 grams |
| Weight of Extracted Eggshells | 22.3 grams | 20.4 grams | 4.1 grams | 7.2 grams | 22.3 grams |
| Percent Eggshell Extracted | 50.68% | 46.36% | 9.3% | 16.36% | 50.68% |
| Initial pH | 2.31 | 2.36 | 3.58 | 3.17 | 3.16 |
| Final pH | 5.88 | 5.82 | 5.26 | 5.54 | 5.08 |
| Calcium Content | 1500 mg/100 g | 1560 mg/100 g | 239 mg/100 g | 336 mg/100 g | 1330 mg/100 g |

LEMON JUICE EGGSHELL CALCIUM EXTRACTION

Eggshell Preparation:

1) Fresh eggs are washed in a mild soap, rinsed with water and allowed to dry at room temperature (70° to 75° F.).
2. After drying, the eggs are cracked and the egg yolks and whites are discarded. The eggshell is then washed thoroughly in mild soap and allowed to dry completely. The drying process generally takes approximately 48 hours.

Fresh Lemon Juice Preparation:

1. Fresh lemons are cut into halves. These halves are then squeezed to extract the juice. An automatic juicer can be used, as well as a small hand juicer.
2. The fresh lemon juice is measured into the appropriate batch size.

*NOTE: The lemon juice is used the same day that it is squeezed.

Reconstituted Lemon Juice:

1. The lemon juice concentrate is stored at 32° F. until needed. It is thawed and reconstituted with 5.8 parts of water to 1 part lemon juice concentrate.

*NOTE: The reconstituted juice is used the same day that it is reconstituted.

Calcium Extraction Method:

1. The prepared lemon juice is poured into large containers and the pH is taken to determine the acidity. A pH in the range of 2.30–2.50 is the ideal pH, and is very important in the effectiveness of the extraction process.
2. The eggshells are weighed.
3. The eggshell halves are then placed into the lemon juice and the mixture is stirred until all of the eggshells are completely covered with the lemon juice. The mixture is stirred slowly, every half hour for the first 2–4 hours in order to ensure coverage of all of the eggshells.

4. When the eggshells are placed into the lemon juice, a reaction will begin to take place almost immediately. Bubbles of carbon dioxide begin floating to the surface of the liquid and a foam will appear at the air/liquid/interface. This reaction is allowed to continue for 22 to 24 hours at room temperature (70°–75° F.).

5. After 22 to 24 hours, the liquid is again stirred and the remaining eggshells are carefully lifted out of the juice mixture. These shells are placed on a tray and allowed to dry. After the shell remnants are dry (this usually takes 24–48 hours), they are weighed in order to determine the amount of the eggshell/calcium that was extracted into the lemon juice.

6. The final percent extraction of the eggshell is calculated. Again, the pH is tested on the lemon juice/eggshell mixture, in order to determine the acidity of the product. The pH should have increased considerably, depending on the amount of calcium extracted into the juice mixture. Generally, a pH of 4.5 to 6.5 is desirable after the eggshell calcium extraction.

7. The mixture is then filtered to remove any large particles of eggshell that might have remained in the bottom of the mixture.

8. The mixture is then immediately transferred to a large kettle, where it is heated to a temperature of 184° F.–190° F., and held at that temperature for five minutes. This is done in order to pasteurize the product for health safety.

9. The mixture is then transferred, while still hot, to sterile gallon containers. These containers are stored in refrigerated storage until the mixture is used in the liquid state or prepared for capsulation by removing the moisture, via freeze drying.

Freeze-Drying:

1. The mixture is transferred from gallon containers into 1 gallon plastic Zip-Loc® bags. These bags are placed into a freezer and allowed to freeze completely solid. This usually takes between 34 and 48 hours.

2. Once frozen, the frozen juice mixture is removed from the Zip-Loc® bags and is placed into sterile metal trays. These trays are placed into a small, non-commercial freeze dryer (it is only non-commercial because of its size and a larger commercial version can be used to dry the product), and remains there until all of the moisture is gone from the product. Once completely dry, the product is a fine yellowish-white powder that can be easily inserted into a capsule for pill consumption.

STIRRED LEMON JUICE EGGSHELL CALCIUM EXTRACTION

Eggshell Preparation:

1. Fresh eggs are washed in a mild soap, rinsed with water and allowed to dry at room temperature (70°–75° F.).

2. After drying, the eggs are cracked and the egg yolks and whites are discarded. The eggshell is then washed thoroughly in mild soap and allowed to dry completely. The drying process generally takes approximately 48 hours.

3. Eggshells are crushed into small pieces (no larger than a ½ cm square).

Fresh Lemon Juice Preparation:

1. Fresh lemons are cut into halves. These halves are then squeezed to extract the juice. An automatic juicer can be used as well as a small hand juicer.

2. The fresh lemon juice is measured into the appropriate batch size.

*NOTE: The reconstituted juice is used the same day that it is reconstituted.

Calcium Extraction Method:

1. The juice is placed in a container that can have any type of mechanical stirrer placed into it.

2. The stirring device is turned on and the juice is allowed to begin stirring. The eggshells are then added to the stirring liquid.

3. The liquid is allowed to stir for a specified amount of time (usually 6 hrs. or overnight).

4. As the eggshells are placed into the lemon juice a reaction will begin to take place almost immediately. Bubbles of carbon dioxide begin floating to the surface of the liquid, and a foam will appear at the air/liquid interface. This reaction is allowed to continue at room temperature 70°–75° F.

5. After the allotted amount of time, liquid is removed from the stirring device and strained through a sieve to remove any remaining eggshells, membrane or large pieces of pulp. The portion of the liquid that is caught in the sieve is placed on a tray and allowed to dry. After the remnants are dry (this usually takes 24–48 hours), they are weighted in order to determine the amount of the eggshell/calcium that was extracted into the lemon juice.

6. The final percent extraction of the eggshell is calculated. Again, the pH is tested on the lemon juice/eggshell mixture in order to determine the acidity of the product. The pH should have increased considerably depending on the amount of calcium extracted into the juice mixture. Generally, a pH of 4.5 to 6.5 is desirable after the eggshell calcium extraction.

7. The mixture is then immediately transferred to a large kettle where it is heated to a temperature of 184° F.–190° F., and held at that temperature for five minutes. This is done in order to pasteurize the product for health safety.

8. The mixture is then transferred while still hot to sterile gallon containers. These containers are stored in refrigerated storage until the mixture is used in the liquid state, or prepared for capsulation by removing the moisture, via freeze drying.

Freeze-Drying:

1. The mixture is transferred from gallon containers into 1 gallon Zip-Loc® bags. These bags are placed into a freezer and allowed to freeze completely solid. This usually takes between 24 and 48 hours.

2. Once frozen, the frozen juice mixture is removed from the Zip-Loc® bags and is placed into sterile metal trays. These trays are placed into a small, non-commercial freeze dryer (it is only non-commercial, because of its size and a larger commercial version can be used to dry the product), and remain there until all of the moisture is gone from the product. Once completely dry, the product is a fine yellowish-white powder than can easily be inserted into a capsule for pill consumption.

LIME JUICE EGGSHELL CALCIUM EXTRACTION

Eggshell Preparation:

1) Fresh eggs are washed in a mild soap, rinsed with water and allowed to dry at room temperature (70° to 75° F.).

2. After drying, the eggs are cracked and the egg yolks and whites are discarded. The eggshell is then washed thoroughly in mild soap and allowed to dry completely. The drying process generally takes approximately 48 hours.

Fresh Lime Juice Preparation:

1. Fresh limes are cut into halves. These halves are then squeezed to extract the juice. An automatic juicer can be used, as well as a small hand juicer.
2. The fresh lime juice is measured into the appropriate batch size.

*NOTE: The lime juice is used the same day that it is squeezed.

Reconstituted Lime Juice:

1. The lime juice concentrate is stored at 32° F. until needed. It is thawed and reconstituted with 5.8 parts of water to 1 part lime juice concentrate.

*NOTE: The reconstituted juice is used the same day that it is reconstituted.

Calcium Extraction Method:

1. The prepared lime juice is poured into large containers and the pH is taken to determine the acidity. A pH in the range of 2.30–2.50 is the ideal pH, and is very important in the effectiveness of the extraction process.
2. The eggshells are weighed.
3. The eggshell halves are then placed into the lime juice and the mixture is stirred until all of the eggshells are completely covered with the lime juice. The mixture is stirred slowly, every half hour for the first 2–4 hours in order to ensure coverage of all of the eggshells.
4. When the eggshells are placed into the lime juice, a reaction will begin to take place almost immediately. Bubbles of carbon dioxide begin floating to the surface of the liquid and a foam will appear at the air/liquid/interface. This reaction is allowed to continue for 22 to 24 hours at room temperature (70°–75° F.).
5. After 22 to 24 hours, the liquid is again stirred and the remaining eggshells are carefully lifted out of the juice mixture. These shells are placed on a tray and allowed to dry. After the shell remnants are dry (this usually takes 24–48 hours), they are weighed in order to determine the amount of the eggshell/calcium that was extracted into the lime juice.
6. The final percent extraction of the eggshell is calculated. Again, the pH is tested on the lime juice/eggshell mixture, in order to determine the acidity of the product. The pH should have increased considerably, depending on the amount of calcium extracted into the juice mixture. Generally, a pH of 4.5 to 6.5 is desirable after the eggshell calcium extraction.
7. The mixture is then filtered to remove any large particles of eggshell that might have remained in the bottom of the mixture.
8. The mixture is then immediately transferred to a large kettle, where it is heated to a temperature of 184° F.–190° F., and held at that temperature for five minutes. This is done in order to pasteurize the product for health safety.
9. The mixture is then transferred, while still hot, to sterile gallon containers. These containers are stored in refrigerated storage until the mixture is used in the liquid state or prepared for capsulation by removing the moisture, via freeze drying.

Freeze-Drying:

1. The mixture is transferred from gallon containers into 1 gallon plastic Zip-Loc® bags. These bags are placed into a freezer and allowed to freeze completely solid. This usually takes between 34 and 48 hours.
2. Once frozen, the frozen juice mixture is removed from the Zip-Loc® bags and is placed into sterile metal trays. These trays are placed into a small, non-commercial freeze dryer (it is only non-commercial because of its size and a larger commercial version can be used to dry the product), and remains there until all of the moisture is gone from the product. Once completely dry, the product is a fine yellowish-white powder that can be easily inserted into a capsule for pill consumption.

STIRRED LIME JUICE EGGSHELL CALCIUM EXTRACTION

Eggshell Preparation:

1. Fresh eggs are washed in a mild soap, rinsed with water and allowed to dry at room temperature (70°–75° C.).
2. After drying, the eggs are cracked and the egg yolks and whites are discarded. The eggshell is then washed thoroughly in mild soap and allowed to dry completely. The drying process generally takes approximately 48 hours.
3. Eggshells are crushed into small pieces (no larger than a ½ cm square).

Fresh Lime Juice Preparation:

1. Fresh limes are cut into halves. These halves are then squeezed to extract the juice. An automatic juicer can be used as well as a small hand juicer.
2. The fresh lime juice is measured into the appropriate batch size.

*NOTE: The reconstituted juice is used the same day that it is reconstituted.

Calcium Extraction Method:

1. The juice is placed in a container that can have any type of mechanical stirrer placed into it.
2. The stirring device is turned on and the juice is allowed to begin stirring. The eggshells are then added to the stirring liquid.
3. The liquid is allowed to stir for a specified amount of time (usually 6 hrs. or overnight).
4. As the eggshells are placed into the lemon juice a reaction will begin to take place almost immediately. Bubbles of carbon dioxide begin floating to the surface of the liquid, and a foam will appear at the air/liquid interface. This reaction is allowed to continue at room temperature 70°–75° F.).
5. After the allotted amount of time, liquid is removed from the stirring device and strained through a sieve to remove any remaining eggshells, membrane or large pieces of pulp. The portion of the liquid that is caught in the sieve is placed on a tray and allowed to dry. After the remnants are dry (this usually takes 24–48 hours), they are weighted in order to determine the amount of the eggshell/calcium that was extracted into the lime juice.
6. The final percent extraction of the eggshell is calculated. Again, the pH is tested on the lime juice/eggshell mixture in order to determine the acidity of the product. The pH should have increased considerably depending on the amount of calcium extracted into the juice mixture. Generally, a pH of 4.5 to 6.5 is desirable after the eggshell calcium extraction.
7. The mixture is then immediately transferred to a large kettle where it is heated to a temperature of 184° F.–190° F., and held at that temperature for five minutes. This is done in order to pasteurize the product for health safety.
8. The mixture is then transferred while still hot to sterile gallon containers. These containers are stored in refrigerated storage until the mixture is used in the liquid state, or prepared for capsulation by removing the moisture, via freeze drying.

Freeze-Drying:

1. The mixture is transferred from gallon containers into 1 gallon Zip-Loc® bags. These bags are placed into a freezer and allowed to freeze completely solid. This usually takes between 24 and 48 hours.

2. Once frozen, the frozen juice mixture is removed from the Zip-Loc® bags and is placed into sterile metal trays. These trays are placed into a small, non-commercial freeze dryer (it is only non-commercial, because of its size and a larger commercial version can be used to dry the product), and remain there until all of the moisture is gone from the product. Once completely dry, the product is a fine yellowish-white powder that can easily be inserted into a capsule or pill for consumption.

The mineral-enriched citrate compositions achieved according to the present invention are to include the following ingredients calculated upon a dry product basis:

| Sugars: | |
|---|---|
| Fructose | 6 g/100 g |
| Glucose | 8 g/100 g |
| Sucrose | 4 g/100 g |
| Acids: | |
| L-Malic acid | 18 g/100 g |
| Malic acid | 1.6 g/100 g |
| Citric acid | 40 g/100 g |
| Isocitric acid | 350 mg/100 g |
| L-ascorbic acid | 250 mg/100 g |
| Minerals: | |
| Potassium | 1400 mg/100 g |
| Sodium | 13 mg/100 g |
| Calcium | 18 g/100 g |
| Magnesium | 170 mg/100 g |
| Phosphorous | 200 mg/100 g |
| Sulfur | 34 mg/100 g |

As will be apparent, the mineral enriched citrate compositions achieved by the present method include not only calcium citrate but also critical trace minerals, namely manganese, magnesium, iron, potassium and phosphorous which are utilized in the body for nail growth. Indeed, it is believed that the trace minerals greatly enhance the absorption of calcium within the human body.

I claim:

1. Method for preparing mineral-enriched citrate compositions for enhancement of fingernail growth, comprising:

a. immersing cracked eggshells within a bath of fruit juice from the group including lemon and lime, having a pH in the range 2.30 to 2.50;

b. stirring the eggshells with the fruit juice until all eggshells are covered with lemon juice; thereafter stirring every half hour for the first 2–4 hours to ensure lemon juice coverage of the eggshells;

c. reacting eggshells and juice as a mixture at ambient temperature (70° to 75° F.), such that the mixture has a pH of 4.5 to 6.5 and over a period of 22–24 hours;

d. removing egg shell residue from the mixture and freeze-drying, so as to remove moisture;

e. heating so as to pasteurize said mixture at 184°–190° F. for approximately five minutes;

f. refrigerating said mixture prior to ingestion, and g. encapsulating said mixture.

* * * * *